United States Patent [19]

Ash et al.

[11] 3,940,404
[45] Feb. 24, 1976

[54] 2-SUBSTITUTED PHENYL-6-TRIFLUOROMETHYL-4-PYRIDYL-CARBINOLAMINES

[75] Inventors: Arthur B. Ash, Detroit; Maurice P. La Montagne, Sterling Heights; Anica Markovac, Lathrup Village, all of Mich.

[73] Assignee: The United States of America as represented by the Secretary of the Army, Washington, D.C.

[22] Filed: Sept. 17, 1974

[21] Appl. No.: 506,684

Related U.S. Application Data

[62] Division of Ser. No. 448,468, March 6, 1974, Pat. No. 3,886,167.

[52] U.S. Cl. ............................. 260/296 R; 424/263
[51] Int. Cl.$^2$ ....................................... C07D 213/36
[58] Field of Search ................................. 260/296 R

[56] References Cited
UNITED STATES PATENTS
3,764,604  10/1973  Ash et al. ..................... 260/296 R

OTHER PUBLICATIONS

La Montagne *J. of Medicinal Chemistry*, Vol. 16, No. 1, (1973), pp. 68–72.

Markovac et al., *J. of Medicinal Chemistry*, Vol. 15, No. 9, (1972), pp. 918–922.

*Primary Examiner*—John D. Randolph
*Assistant Examiner*—B. Dentz
*Attorney, Agent, or Firm*—Miller, Morriss, Pappas & McLeod

[57] ABSTRACT

A series of 2-aryl-6-trifluoromethyl-4-pyridylcarbinolamines is herein disclosed which has value in treatment of plasmodial infections. The compounds have substituted phenyl groups at position 2- on the pyridine moiety, with the electronegative substituents present on the phenyl nuclei. The syntheses of such series is described, together with a method for separation of racemates of a representative 4-pyridylcarbinolamine type.

5 Claims, No Drawings

2-SUBSTITUTED PHENYL-6-TRIFLUOROMETHYL-4-PYRIDYL-CARBINOLAMINES

This is a division of application Ser. No. 448,468 filed Mar. 6, 1974 now U.S. Pat. No. 3,886,167.

BACKGROUND OF THE INVENTION

The subject invention relates to 2-aryl-6-trifluoromethyl-4-pyridinecarbinolamines having enhanced antimalarial activity, and to means for achieving the synthesis of such compounds. Specifically, the new products are 6-trifluoromethyl-pyridine-4-carbinols bearing a basic function in the alpha-position, and having a substituted-phenyl grouping at position 2-on the pyridine moiety. For convenience in administration as well as stability under storage, it is preferred that subject bases be transformed into acid-addition salts with pharmaceutically acceptable inorganic or organic acids.

Prior investigations have demonstrated that certain substituted aminomethyl-2,6-substituted phenyl 4-pyridine carbinols have antimalarial activity. The present invention reltes to representatives which differ structurally from those known hitherto particularly because they have a trifluoromethyl group in the 6-position, and provide advantages in chemotherapeutic index and also in potential for avoiding unwanted side effects such as photoxicity.

DETAILED DISCLOSURE OF THE INVENTION

The subject series of carbinolamine types is conveniently represented by the Structure I, and to pharmaceutically-acceptable acid-addition salts thereof which also form basis for the invention. It is intended that there be included the several isomeric forms possible in Structure I, moreover.

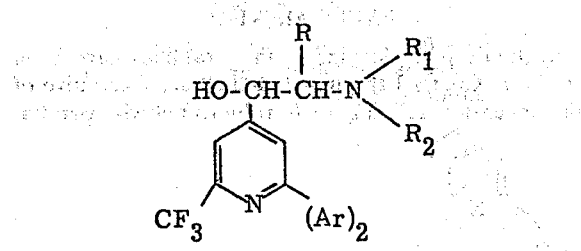

The above (Structure I) establishes the new antimalarial agents as pyridine-4-carbinols bearing a basically-substituted unit in the alpha-position, and the substituted-phenyl grouping on the 2-pyridine ring system. This comes from definition of terms, wherein, $R$ = hydrogen, while
$R_1$ = hydrogen, or (lower alkyl) and
$R_2$ = (lower alkyl), the same or different from $R_1$; or,
$R + R_1 = -(CH_2)_4-$, with $R_2 = H$; and
$(Ar)_2$ is substituted-phenyl groupings. The term lower alkyl as used herein means 1 to 10 carbon atoms which can be straight, branched chain or with sufficient carbon atoms cyclic with repeating methylene groups.

The patterns of worth for representatives of Structure I have been established through use of highly standardized tests in experimental mammals. The preferred mode for administering these compounds consists in use of non-toxic acid-addition salts, inclusive of those formed from (I) and acids such as hydrochloric, hydrobromic, sulfamic, sulfuric, phosphoric, citric, tartaric, methanesulfonic, isethionic, aceturic, malic, fumaric, beta-resorcylic, or pamoic acid. Said salts may be administered orally in the form of tablets, capsules, or dragees when admixed with solid excipients such as lactose, sucrose, starch, microcrystalline cellulose, magnesium stearate or talc. The foregoing compositions are preferred means for oral administration over use of flavored syrups or tinctures containing the antimalarial drug. Under special circumstances, parenteral administration may be indicated, employing an aqueous solution of the agent or an oleaginous formulation of it. Aqueous solutions can be prepared in water, physiological saline, Ringer's solution, or the like, either with or without buffers. Oleaginous formulations may be made in natural oils (as, peanut oil or olive oil), or in benzyl benzoate, for example. The several possible isomeric forms for Structure I are to be included among the preferred antimalarials, and advantage may accrue in the choice of one or other of these.

This invention includes mode for the chemical synthesis of the series defined by Structure I. Charts 1 through 3 have been used to outline the synthesis of the subject carbinolamines. As is apparent from the structure, such series occur in optically active form. A representative type, where two optical centers are present, has been separated into a pair of racemates, one of which has appreciable antimalarial activity.

The course of synthesis of alpha-(dialkylaminomethyl)-2-aryl-6-trifluoromethyl-4-pyridinecarbinols (Structure I, R = H, having $R_1$ and $R_2$ as lower alkyl groupings, with $(Ar)_2$ as a substituted phenyl group) is outlined in Chart 1.

CHART I

Alpha-(Dialkylaminomethyl)-2Aryl-6-Trifluoromethyl-4-Pyridinecarbinols

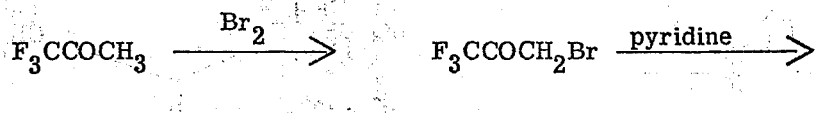

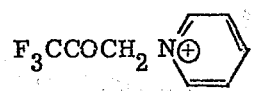

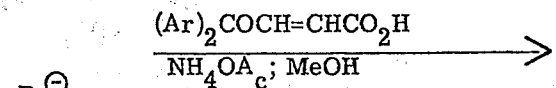

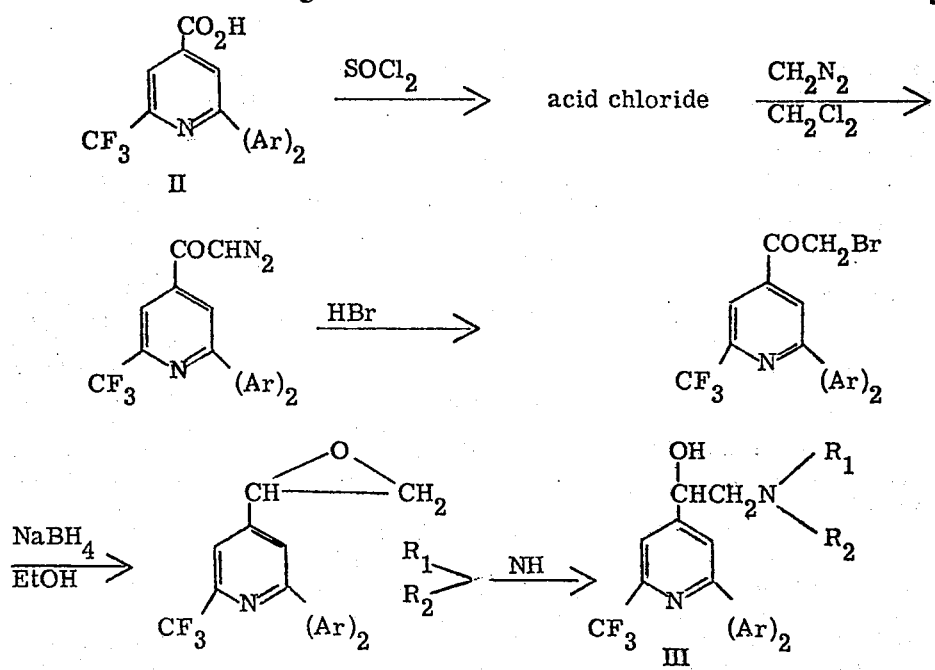

The requisite products have Formula III. The intermediate oxirane could be caused to react with various primary amines ($R_1$ = H; $R_2$ = alkyl) or secondary amines ($R_1$ and $R_2$, each, being alkyl groupings) the same or different. Said carbinolamines (Formula III) were most satisfactorily administered in the form of acid-addition salts.

The requisite alpha-(2-piperidyl)-2-aryl-6-trifluoromethyl-4-pyridylcarbinols (Formula IV) were prepared from the intermediate 2-aryl-6-trifluoromethyl-isonicotinic acids (Formula II) in the manner outlined in Chart 2.

CHART 2
Alpha-(2-Piperidyl)-2-DiAryl-6-Trifluoromethyl-4-Pyridylcarbinols

The Examples hereinafter given further illustrate the preparation of 2-aryl-6-trifluoromethyl-4-pyridylcarbinolamines of Formula I, but in no way limit the scope of the Invention to Formulas III and IV as representative thereof. Said representations are not to be viewed as restricted to a single stereoisomeric form. All temperatures are given in degrees Celsius (°C), and metric units are employed for weights and measures. The designation of the trifluoromethyl group could be either in the 6-or 2- position with the aryl group in the other position.

EXPERIMENTAL

Synthetic paths leading to the Examples have been shown in Charts 1 through 3, and all are illustrative of the Invention relating to 6-trifluoromethyl-4-pyridyl-

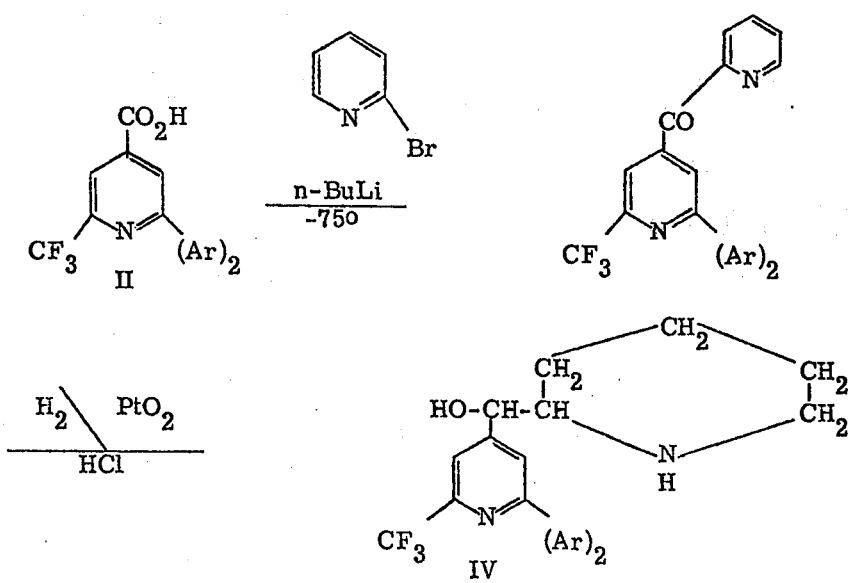

As in the instance of the less complex carbinolamines (Chart 1), so also the products (Formula IV) of transformations given in Chart 2 were most conveniently used in the form of their acid-addition salts.

carbinolamines having Formula I. Based upon the testing results with the 2-(trifluoromethylphenyl) compounds of Examples I to X, the corresponding chloro, bromo, fluoro and methoxy or alkoxy compounds would also be active antimalarials in the same manner as in Ser. No. 150,745 now U.S. Pat. No. 3,764,604 referred to above. Alternative routes for acquiring certain intermediates are apparent to those skilled in the art, and certain of these are revealed in the examples.

EXAMPLE I

Alpha-n-Butyaminomethyl-2-(4-trifluoromethylphenyl)-6-trifluoromethyl-4-pyridylcarbinolamine Hydrochloride Trifluoromethylacylpyridinium Bromide 1,1,1-Trifluoro-3-bromoacetone (60 g) was converted to the pyridinium salt (63 g, 70%), mp 189°–191° ($CH_3CN$).

3-(4-Trifluoromethylbenzoyl)acrylic Acid

Freshly fused $ZnCl_2$ (82 g, 0.6 mole) was dissolved in dry $Et_2O$ (400 ml) and added dropwise to the Grignard reagent prepared from 4-bromobenzotrifluoride (112.5g, 0.5 mole) and Mg (12.2 g, 0.5 g-atom) in $Et_2O$ (600 ml). Maleic anhydride (44 g, 0.45 mole) in $Et_2O$ (400 ml) was added over 30 minutes with stirring at reflux. After 2 hours, the mixture was cooled and acidified to pH 2 with 10% HCl. The $Et_2O$ layer was separated and dried ($MgSO_4$), and the $Et_2O$ evaporated. The residue was recrystallized from $C_6H_6$(x3) to yield the title compound, 24.5 g (21%), mp 149°–151°. Anal. ($C_{11}H_7F_3O_3$) C, H, F. An alternative procedure is as follows. A mixture of 4-trifluoromethylacetophenone (18.8 g) glyoxylic acid monohydrate (18.8 g), $Ac_2O$(20 ml) and a drop of $Et_3N$ was heated to 135°, internal temperature. More $Et_3N$ (2 ml) was added, and the mixture was held at 135° for 20 minutes. The mixture was cooled and evaporated to dryness in vacuo. The solid residue was digested with $H_2O$, filtered, dried and recrystallized from $C_6H_6$ to give the title compound, 12.2 g (50%), mp 149°–151°.

This procedure required close temperature control to avoid tar formation. To avoid this, the method was modified to a two-step process wherein the intermediate alpha-hydroxy acid was isolated and pyrolyzed separately. 4-Trifluoromethylacetophenone (75.2 g, 0.4 mole) and $OHCCO_2H.H_2O$ (75.2 g) were heated neat at 79°–80° for 8 hr. The hot mixture was poured into diluted aqueous HCl (7.5 ml of concd HCl and 800 ml of $H_2O$) with stirring. The aqueous mixture was extracted with $Et_2O$ (2 × 250 ml), and the aqueous phase was discarded. The extract was washed with $H_2O$ (2 × 100 ml), and dried ($Na_2SO_4$), and $Et_2O$ was removed (aspirator). The resulting residue was digested with hot $CHCl_3$(100 ml) and the mixture was concentrated to a volume of 80–85 ml. Petroleum ether (30°–60°, 250 ml), was added with stirring. The resulting precipitate was collected and washed with petroleum ether (100 ml). (Removal of petroleum ether from the combined washes and filtrate yielded unreacted acetophenone, 39.3 g, 52.3%, suitable for recycling.) The solid was digested again with $CHCl_3$ (150 ml), filtered, and air-dried to yield 2-hydroxy-3-(4-trifluoromethylbenzoyl)-propionic acid (31.2 g, 62%), mp 118°–120°. anal. ($C_{11}H_9F_3O_4$) C, H. The alpha-hydroxy acid was heated neat under vacuum (1–2 mm) in an oil bath until the internal temperature reached 155°. The temperature was increased to 160° over 40 minutes to complete the elimination of $H_2O$. The flask was allowed to cool and crystallization of the title acrylic acid usually began at around 138°. The product was sufficiently pure for conversion to isonicotinic acid.

2-Trifluoromethyl-6-(4-trifluoromethylphenyl)isonicotinic Acid

The pyridinium salt (2.7 g), 3-(4-trifluoromethylbenzoyl)arcylic acid (12.6 g) and $NH_4OAc$ (6 g) in MeOH (100 ml) were refluxed 8 hours. The mixture was evaporated to dryness. The residue was boiled with 20% AcOH and refrigerated. The precipitate was crystallized from $C_6H_6$ to yield the title acid (2 g, 56%), mp 204°–205°.

Anal. Calcd for $C_{14}H_7F_6NO_2$: C, 50,16; H, 2.11; N, 4.18. Found: C, 50,50; H, 2.19; N, 4.23.

4-Epoxyethyl-2-(4-trifluoromethylphenyl)-6-trifluoromethylpyridine

A suspension of the isonicotinic acid (3.6 g) in $SOCl_2$ (50 ml) was refluxed 2 hours. The excess of $SOCl_2$ was evaporated and the crude acid chloride was converted to the diazoketone. The crude, oily diazoketone (3.1 g, 80%) was dissolved in $CH_2Cl_2$ (100 ml) and converted to the bromoketone with 48% HBr (5ml) in AcOH (60 ml). The crude bromoketone (2.6 g, 74%), an oil was dissolved in EtOH (100 ml) and reduced with $NaBH_4$ (300 mg) to yield the crude title epoxide (1.45 g, 70%), mp 184°–186°, usable for subsequent conversions to target aminoalcohols as described below.

Alpha-n-Butylaminomethyl-2-(4-trifluoromethylphenyl)-6-trifluoromethyl-4-pyridylcarbinolamine Hydrochloride The crude epoxide (1.45 g, 70%) was dissolved in EtOH (50 ml) and refluxed with n-butylamine (5 ml) for 8 hours. The mixture was evaporated. The residue was dissolved in $Et_2O$, washed with $H_2O$, dried ($K_2CO_3$) and the solution was evaporated. The crude free base was dissolved in $CH_3CN$ and acidified with dry HCl. The solution was evaporated and the residue was crystallized from $CH_3CN$ to give the title compound (0.7 g, 32%), mp 184°–186°.

Anal. Calcd $C_{20}H_{21}ClF_6N_2O$: C, 51.02; H, 4.56; N, 6.01. Found: C, 51.07; H, 4.82; N, 6.25.

EXAMPLE II

Alpha-4'-Heptylaminomethyl-2-(4-trifluoromethylphenyl)-6-trifluoromethyl-4-pyridylcarbinolamine Hydrochloride A solution of the epoxide (3.6 g, 0.011 mol) in EtOH (100 ml) from Example I containing 4-aminoheptane (7 g) was refluxed 17 hours. The solvent and excess amine were removed under reduced pressure. The residual oil was dissolved in $Et_2O$ and $Et_2O$—HCl was added to pH 2. The mixture was filtered to remove a little 4-aminoheptane HCl. The filtrate was concentrated to dryness. The residual solid was slurried in fresh $Et_2O$ and filtered to afford the crude target compound (2.8 g, 53%). Recrystallization from $CH_3CN$ (×2) gave the title compound (1.5 g, 28%), mp 183°–184°.

Anal. Calcd for $C_{22}H_{27}ClF_6N_2O$: C, 54.50; H, 5.60; Cl, 7.30; N, 5.80. Found: C, 54.74; H, 5.67; Cl, 7.19; N, 5.75.

EXAMPLE III

Alpha-Di-n-butylaminomethyl-2-(4-trifluoromethylphenyl)-6-trifluoromethyl-4-pyridylcarbinolamine Hydrochloride A solution of the epoxide (3.6 g, 0.011 mol) of Example I in EtOH (100 ml) and di-n-butylamine (7 ml)

was refluxed 17 hr. The solution was concentrated to dryness under the reduced pressure. The residual oil was dissolved in Et$_2$O and Et$_2$O—HCl was added to pH 2. A little di-n-butylamine hydrochloride was removed by filtration and the filtrate was concentrated to dryness to give crude HCl salt. This was isolated as the free base by stirring with 5% aqueous KOH, extracting with Et$_2$O and evaporating. The residue was placed onto a silica gel column and eluted with C$_6$H$_6$—MeOH (97:3, v/v). The fast moving band was collected as an oil (3.2 g). This oil was dissolved in MeOH and concentrated HCl (1 eq) was added. The solution was concentrated to dryness. The residual solid was crystallized from Et$_2$O-petroleum ether ($\times$1) and CHCl$_3$-petroleum ether ($\times$1). The precipitate was stirred in warm H$_2$O ($\times$2). The washed solid (1.3 g) was dissolved in Et$_2$O (60 cc) and filtered. Petroleum ether was added to the filtrate until the solution became faintly turbid. The crystals which formed were filtered and dried to afford the target compouund (1.0 g, 18%), mp 128°–129.5°.

Anal. Calcd for C$_{23}$H$_{29}$ClF$_6$N$_2$O: C, 55.37; H, 5.86; Cl, 7.10; N, 5.61. Found: C, 55.22; H, 6.00; Cl, 6.94; N, 5.70.

EXAMPLE IV

Synthesis of
Alpha-n-butylaminomethyl-2-(2-trifluoromethylphenyl)-6-trifluoromethyl-4-pyridinemethanol Beta-(2-Trifluoromethylbenzoyl)acrylic Acid A mixture of 2-trifluoromethylacetophenone (50 g, 0.266 mole) and glyoxylic acid hydrate (50 g) was heated at 100° for 23 hours. The reaction mixture was poured into 400 ml of H$_2$O containing 18 ml of HCl with stirring. The mixture was extracted with Et$_2$O ($\times$2). The Et$_2$O extract was washed with H$_2$O and the Et$_2$O was removed under reduced pressure. The residue was azeotroped with CHCl$_3$ and then stirred with petroleum ether ($\times$3) to remove unreacted starting compound (11 g). Removal of petroleum ether gave 48.5 g of an oily residue which, by thin layer chromotography (tlc—MeOH/CHCl$_3$/NH$_4$OH, 3 ml:1 ml:5 drops) showed 90% of product and 10% of beta-(2-trifluoromethylbenzoyl)-alpha-hydroxypropionic acid. The oily residue was heated at 160° (2 mm) for 20 min to give 37 g(74%, based on converted 2-trifluoromethylacetophenone) of syrupy residue which, by tlc (same system described previously), showed more than 90% of the title acid. The compound was used as such for the next reaction.

2-(2-Trifluoromethyphenyl)-6-trifluoromethylisonicotinic Acid.

A solution of beta-(2-trifluoromethylbenzoyl)acrylic acid (18.0 g, 0.075 mole), trifluoromethylacylpyridinium bromide (19.2 g) and NH$_4$OAc (60g) in MeOH (150 ml) was heated at reflux overnight. HOAc (60 ml) was added followed by H$_2$O ($\times$1) and then extracted with 5% aqueous KOH ($\times$2, 150 ml). The aqueous layer was separated and acidified to pH 2 with HCl. The mixture was then extracted with CHCl$_3$ ($\times$2). The organic layer was dried (MgSO$_4$) and concentrated at reduced pressure. The residue crystallized on standing. The solid was triturated in toluene (30 ml), cooled and filtered to give the isonicotinic acid (10.8 g, 44%), mp 155°–157°. A sample was recrystallized from toluene, mp 156°–158°.

Anal. Calcd for C$_{14}$H$_7$F$_6$NO$_2$: C, 50.16; H, 2.10; N, 4.18. Found: C, 50.05; H, 2.25; N, 4.16.

Bromomethyl 2-(2-Trifluoromethylphenyl)-6-trifluoromethyl-4-pyridyl Ketone.

A solution of the above isonicotinic acid (5.0 g, 0.015 mole) in SOCl$_2$ (55 ml) was heated at reflux 3 hours. The excess SOCl$_2$ was removed under reduced pressure. The crude acid chloride (5 g) was added to a solution of CH$_2$N$_2$ (ca. 5 g) in Et$_2$O (300 ml) at 0°–5°. The resulting solution was stirred at 0° for 3 hours. The solvent and excess CH$_2$N$_2$ were removed under reduced pressure to afford the diazoketone as an oil (ca. 5 g).

A solution of this crude diazoketone in CHCl$_3$ (10 ml) was added to a mixture of 48% HBr (12 ml) and HOAc (10 ml) at 0°–5°. The mixture was warmed to room temperature and stirred an additional 0.5 hour. CHCl$_3$ was added and the mixture was washed with H$_2$O ($\times$2) and diluted aqueous K$_2$CO$_3$ ($\times$1). The CHCl$_3$ was dried (MgSO$_4$) and concentrated to give the bromoketone as an oil which could not be crystallized. The oil was purified by passage over a silica gel column elution with C$_6$H$_6$/petroleum ether (3:2). The material obtained (46 g, 75%) was homogeneous on tlc (C$_6$H$_6$/MeOH, 95:5).

Alpha-n-Butylaminomethyl-2-(2-trifluoromethylphenyl)-6-trifluoromethyl-4-pyridylcarbinolamine Hydrochloride To a solution of above bromoketone (4.6 g, 0.011 mole) of Example IV in EtOH (40 ml) and 2-ethoxyethanol (10 ml) at −25° was added NaBH$_4$ (0.43 g) in H$_2$O (5 ml). The solution was warmed to room temperature and stirred an additional 1 hour, after which time a solution of KOH (0.45g) in EtOH was added. The solution was stirred at room temperature 0.5 hours. The solution was diluted with H$_2$O and the mixture was extracted with CHCl$_3$ ($\times$2). The CHCl$_3$ was dried (MgSO)$_4$ and concentrated to afford crude epoxide which was purified by chromatography over a silica gel column and elution with C$_6$H$_6$. The product (3.0 g, 82%) was obtained as an oil.

A solution of the epoxide (1.5 g, 4.5 mmole) in EtOH (40 ml) containing n-BuNH$_2$ (3.5 ml) was heated at reflux 17 hours. The solvent and excess amine were removed under reduced pressure to afford an oil which crystallized on standing. This solid was dissolved in CH$_3$CN (15 ml) and concentrated HCl (0.37 ml) was added. The solid was filtered to yield the target compound (1.3 g, 65%, mp 184°–186°.

Anal. Calcd for C$_{19}$H$_{21}$ClF$_6$N$_2$O; C, 51.53; H, 4.78; N, 6.33; Cl, 8.01. Found: C, 51.30, H, 4.92; N, 6.32; Cl 8.05.

EXAMPLE V

Alpha-Di-n-butylaminomethyl-2-(2-trifluoromethylphenyl)-6-trifluoromethyl-4-pyridylcarbinolamine Hydrochloride.

The epoxide (1.5 g, 4.5 mmole) of Example IV was treated with n-Bu$_2$NH (3.5 ml) in EtOH (35 ml) as described above. The crude free base (oil) was dissolved in Et$_2$O and Et$_2$O/HCl was added to pH 2. The Et$_2$O was concentrated and the residue was triturated in fresh Et$_2$O. A little n-Bu$_2$ NH . HCl was removed by filtration. The Et$_2$O was concentrated and the residue was dissolved in MeOH. HCl (1 eq) was added and the MeOH was removed to afford a glass. This solid could be crystallized from Et$_2$O — petroleum ether to give the product (1.3 g) contaminated with a little n-Bu$_2$ NH . HCl. This solid was slurried in $H_2O$ to give pure target compound (0.9 g, 40%), mp 120°–122°.

Anal. Calcd for $C_{23}H_{24}ClF_6N_2O$: C, 55.37; H, 5.86; Cl, 7.10; N, 5.61. Found: C, 55.14; H, 5.96; Cl, 7.03; N, 5.72.

EXAMPLE VI

Synthesis of Alpha-n-Butylaminomethyl-2-trifluoromethyl-6-(3-trifluoromethyl)-4-pyridylcarbinolamine Hydrochloride Beta-(3-Trifluoromethylbenzoyl)acrylic Acid A mixture of 3-trifluoromethyl-acetophenone (20 g, 0.106 mole) and glyoxylic acid hydrate (20 g) was heated at 80° for 8 hours. The reaction mixture was poured into $H_2O$ (160 ml) containing HCl (6 ml) and extracted with $Et_2O$ (×2). The combined $Et_2O$ extracts were washed with $H_2O$ and the $Et_2O$ was removed under reduced pressure. The residue (26.4 g) solidified after azeotroping with $CHCl_3$ and then stirring with petroleum ether (30°–60°) to remove the unreacted starting acetophenone. Tlc ($MeOH/CHCl_3/NH_4OH$, 12:4:1) of the residue showed it to be a mixture of acrylic acid (40%) and hydroxy acid (60%). The residue was then heated at 160° (2 mm) for 40 minutes to obtain 21.9 g of oily product which was ca. 90% acrylic acid by tlc. The crude acrylic acid was used as such in the next reaction. An analytically pure sample was recrystallized from $C_6H_6$(×2), mp 114°–115°.

Anal. Calcd for $C_{11}H_7F_3O_3$: C, 54.11; H, 2.89. Found, C, 54.31; H, 3.18.

2-Trifluoromethyl-6-(3-trifluoromethylphenyl)isonicotinic Acid

A mixture of Beta-(3-trifluoromethylbenzoyl)acrylic acid (21.9 g, 0.079 mole), trifluoromethylacylpyridinium bromide (21 g, 0.078 mole) and $NH_4OAc$ (46 g) in MeOH (470 ml) was refluxed 8 hours. The solution was evaporated to dryness and the residue was treated with AcOH (20 ml) and then taken up in $CHCl_3$. The $CHCl_3$ solution was washed with $H_2O$ (×3) and then extracted with 10% aqueous NaOH (×3). After acidifying with HCl, the solution was extracted with $CHCl_3$(×3). Upon cooling the $CHCl_3$ solution, the crystalline product precipitated. The crude product was collected and recrystallized from $C_6H_6$ affording 4.4 g (16%) of product, mp 185°–186°.

Anal. Calcd for $C_{14}H_7F_6NO_2$: C, 50.16; H, 2.10; N, 4.18. Found: C, 50.17; H, 2.24; N, 4.26.

Bromomethyl 2-Trifluoromethyl-6-(3-trifluoromethylphenyl)-4-pyridyl Ketone

A solution of the above isonicotinic acid (4 g, 0.011 mole) and $SOCl_2$ (45 ml) was refluxed 2 hours. The solution was concentrated. The residue was suspended in $C_6H_6$ and the solvent was evaporated. The crude acid chloride was dissolved in anhydrous $Et_2O$ (50 ml) and added to a solution of $CH_2N_2$ (5 g) in $Et_2O$ (300 ml) at 0°. After refrigeration for 2 hours, the solvent and excess $CH_2N_2$ were evaporated. The crude diazoketone (4.6 g) was dissolved in $CHCl_3$ (25 ml) and added to a mixture of 48% HBr (10 ml) and AcOH (90 ml) at 5°. The solution was washed with $H_2O$ and aqueous $NaHCO_3$. After drying ($K_2CO_3$), the solution was concentrated to give an oily residue which crystallized on standing. Recrystallization from $EtOH/H_2O$ gave pure product (2.0 g, 41%), mp 87°–89°.

Anal. Calcd for $C_{15}H_8BrF_6NO$: C, 43.72; H, 1.96; N, 3.40. Found: C, 43.83; H, 2.20; N, 3.42.

Alpha-n-Butylaminomethyl-2-trifluoromethyl-6-(3-trifluoromethylphenyl)-4-pyridylcarbinolamine Hydrochloride A solution of $NaBH_4$ (0.19 g, 0.005 mole) in $H_2O$ (2 ml) was added to a solution of the bromoketone (2.0 g, 0.0045 mole) in EtOH (30 ml) and 2-ethoxy-ethanol (10 ml) at −25°. The resulting solution was stirred at room temperature for 1 hour. A solution of KOH (0.19 g) in 3 ml of EtOH was added and the reaction mixture was stirred for another 0.5 hours. The mixture was diluted with $H_2O$ and dried ($MgSO_4$). The solvent was evaporated to give crude epoxide (1.6 g). The epoxide (1.6 g) was dissolved in EtOH (30 ml), n-$BuNH_2$ (3.5 ml) was added and the solution was refluxed overnight. The solution was evaporated to dryness. The solid residue was dissolved in $CH_3CN$ and 1 eq of concentrated HCl (0.36 ml) was added. The precipitate was collected and recrystallized from $CH_3CN$ to afford 1.2 g (60%) of product as colorless crystals, mp 215°–216°.

Anal. Calcd for $C_{19}H_{21}ClF_6N_2O$: C, 51.35; H, 4.78; Cl, 8.00; N, 6.33. Found: C, 51.34; H, 4.97; Cl, 8.10; N, 6.21.

EXAMPLE VII

Alpha-Diisopentylaminomethyl-2-(4-trifluoromethylphenyl)-6-trifluoromethyl-4-pyridylcarbinolamine Hydrochloride The title compound was prepared according to the procedure described for Example I. From 2-(4-trifluoromethylphenyl)-6-trifluoromethyl-4-pyridylethylene oxide (2.5 g), EtOH (40 ml) and diisopentylamine (3 ml) was obtained the target compound (2.1 g, 40%), mp 138°–141° ($Et_2O$/petroleum ether).

Anal. Calcd for $C_{25}H_{32}F_6N_2o$ . HCl: C, 56.98; H, 6.31; N, 5.31; F, 21.63. Found: C, 57.26; H, 6.36; N, 5.60; F, 21.44.

EXAMPLE VIII

Alpha-(2-piperidyl)-2-(4-trifluoromethylphenyl)-6-trifluoromethyl-4-pyridylcarbinolamine Hydrochlorides Racemate A Anhydrous $Et_2O$ (20 ml) was cooled to 0° under $N_2$. n-Butylithium (1.6 M, 13 ml, 21 mmol) was added and the solution was cooled to −75°. To this solution was added 2-bromopyridine (3.16 g, 20 mmol). The solution was stirred at −70° for 1 hour and 2-(4-trifluoromethylphenyl)-6-trifluoromethylisonicotinic acid (3.35 g, 0.01 mol) was added. The solution was stirred at −70° for 2 hours. The mixture was allowed to warm to −5° and poured into ice $H_2O$ (120 ml) with stirring. After stirring for 15 minutes, the mixture was extracted (×2) with $Et_2O$. The organic layer was separated, dried ($MgSO_4$) and evaporated in vacuo to give a dark oil. Trituration with 70% aqueous i-PrOH gave dark crystals. Recrystallization from 65% aqueous i-PrOH gave 2-(4-trifluoromethylphenyl)-6-trifluoromethylisonicotinoyl 2′-pyridyl ketone (1.6 g, 41%), mp 85°–87°.

Anal. Calcd for $C_{18}H_{10}N_2F_6O$: C, 57.59; H, 2.54; N, 7.07; F, 28.76 Found: C, 57.70; H, 2,82; N, 7.24; F, 28.98.

In a Parr hydrogenation apparatus, the above ketone (1.6 g, 4 mmol) was hydrogenated over Pt from $O_2$ (150 mg) containing concentrated aqueous HCl (0.6 ml) at room temperature and 45 psig for 16 hours (100% uptake). The catalyst was filtered and the filtrate was concentrated to dryness under reduced pressure. The cruude product was suspended in Et$_2$O, evaporated to dryness and the residue was recrystallized from hot CH$_3$CN (ca. 5 ml). After refrigeration, the precipitate was separated (ca. 1 g) and recrystallized from CH$_3$CN to yield the title compound (850 ml), mp 170°–172°. The compound was pure Racemate A by tlc analysis (CHCl$_3$—EtOH—Et$_3$N, 8:1:1). Recrystallization again from CH$_3$CN gave an analytical sample, mp 172°–174°.

Anal. Calcd for C$_{19}$H$_{19}$ClF$_6$N$_2$O: C, 51.77; H, 4.34; N, 6.35; Cl, 8.04. Found: C, 51.49; H, 4.31; N, 6.46; Cl, 8.28.

The HCl salt (100 mg) was suspended in Et$_2$O and treated with 5% aqueous NaOH. The Et$_2$O layer was separated, dried (K$_2$CO$_3$) and the solvent was evaporated. The residue was recrystallized from Et$_2$O-petroleum ether (30°–60°) to yield the free base (75 mg), mp 140°–142°.

EXAMPLE IX

Racemate B

Acetylation of the free base of Racemate A (800 mg) with Ac$_2$O (210 mg) in Me$_2$CO solvent (6 ml) was complete after 4 hours by tlc. The solution was evaporated and the crude N-actyl derivative was heated overnight with SOCl$_2$ (5 ml). After removal of excess SOCl$_2$, the residue was treated with 6 N HCl and stirred 3 hours (steam bath). The colorless precipitate was recrystallized from 6 N HCl to yield the title compound, Racemate B, HCl salt (600 mg, 69%,) mp 232°–234°, one spot on tlc, same system.

Anal. Calcd for C$_{19}$H$_{19}$ClF$_6$N$_2$O: C, 51.77; H, 4.34; N, 6.35; Cl, 8.04. Found: C, 51.51; H, 4.60; N, 6.40; Cl, 8.07.

EXAMPLE X

Alpha-(3-Pentylaminomethyl)-2-(4-trifluoromethylphenyl)-6-trifluoromethyl-4-pyridylcarbinolamine Hydrochloride A solution of the ethylene oxide of Example I (2.5 g) was heated at reflux in EtOH (50 ml) containing 3-aminopentane (3.5 ml) for 17 hours. The solvent and excess amine were removed under reduced pressure. The residual solid was dissolved in Et$_2$O and Et$_2$O/HCl was added to pH 2. The solid was filtered, washed with H$_2$O and recrystallized from CH$_3$CN (×2) to afford the title compound (1.5 g, 43%), mp 196°–198°.

Anal. Calcd for C$_{20}$H$_{23}$ClF$_6$N$_2$O: C, 52.58; H, 5.07; F, 24.95; N, 6.13. Found: C, 52.85; H, 5.12; F, 24.66; N, 6.42.

The following Table illustrates the antimalarial activity of the compounds of the present invention set forth in Examples I to X. These compounds are distinguished in that they produce cures in mice against *P. berghei*.

TABLE I 2-(2, 3 or 4-Trifluoromethylphenyl)-6-Trifluoromethyl-4-Pyridine methanols

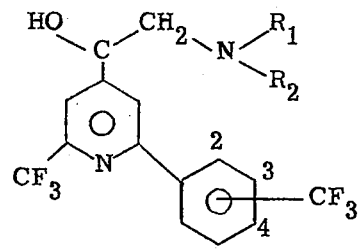

| Examples | Position of CF$_3$ on Phenyl | R$_1$ | R$_2$ | Rane Data Δ$^{(a)}$MST, Days at MPK C = Cure, A = Active(Alive Day 14) | | | | |
|---|---|---|---|---|---|---|---|---|
| | | | | 5 | 10 | 20 | 40 | 80 |
| I | 4- | H | 1-Butyl | 4.7 | 8.7 | 14.1 | 3C | 4C |
| II | 4- | H | 4-Heptyl | 3.3 | 7.9 | 3C | 5C | 5C |
| III | 4- | 1-Butyl | 1-Butyl | | | 3.8 | 11.5 | 3C | 5C |
| IV | 2- | H | 1-Butyl | | | 1.0 | 6.8 | 13.3 | 3C |
| V | 2- | 1-Butyl | 1-Butyl | Inactive at low dosages, active at 640 MPK | | | | |
| VI | 3- | 1-Butyl | 1-Butyl | | 2.9 | 7.7 | 14.1 | 3C |
| VII | 4- | Isopentyl | Isopentyl | | | 3.7 | 5A | 5A |
| VIII | 4- | α-Pip, rac A | (R$_1$+R$_2$) | | 0.3 | 10.9 | 5C | 5C |
| IX | 4- | α-Pip, rac B | (R$_1$+R$_2$) | 0.5 | 11.7 | 5C | 5C | 5C |
| X | 4- | H | 3-Pentyl | | | | 14.3 | | a. Test method described by T. S. Osdene, P. B. Russell, and L. Rane, *J. Med. Chem.*, 10, 431 (1967). This test has been made as a highly standardized procedure in which the *P. berghei* causes death of control mice at essentially 6.2 days. An increase in survival of mice by more than 2.5 days beyond this time has been found to be statistically significant. Mice which live more than 60 days are regarded as cured (C). Drugs which prolong the life of the mice beyond 14 days are considered active (A). Groups of five mice have been used at each dose level of the drugs.

We claim:
1. Compound of the formula

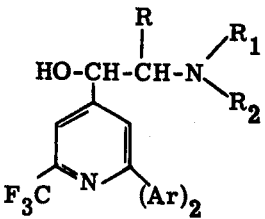

and pharmaceutically acid addition salts thereof wherein
R is hydrogen, while
R$_1$ is hydrogen, lower-alkyl, or cycloalkyl of 3 to 10 carbon atoms
R$_2$ is lower-alkyl or cycloalkyl of 3 to 10 carbon atoms, R$_2$ being the same or different as R$_1$; and
(Ar)$_2$ is phenyl substituted by one trifluoromethyl, chloro, bromo, fluoro or methoxy substituent in the phenyl ring.

2. The compound according to claim 1 wherein (Ar)$_2$ is the trifluoromethyl substituted phenyl group.

3. The compound of claim 1, 2-(4-trifluoromethylphenyl)-6-trifluoromethyl-4-alpha-(n-butylamino)methylpyridine carbinol and pharmaceutically acceptable acid addition salts thereof.

4. The compound of claim 1, 2-(4-trifluoromethylphenyl)-6-trifluoromethyl-4-alpha-(4-heptylamino)methyl pyridine carbinol and pharmaceutically acceptable acid addition salts thereof.

5. The compound of claim 1, 2-(4-trifluoromethylphenyl)-6-trifluoromethyl-4-alpha-(di-n-butylamino)methyl pyridine carbinol and pharmaceutically acceptable acid addition salts thereof.

* * * * *

UNITED STATES PATENT OFFICE
CERTIFICATE OF CORRECTION

PATENT NO. : 3,940,404

DATED : February 24, 1976

INVENTOR(S) : Arthur B. Ash, Maurice P. LaMontagne & Anica Markovac

It is certified that error appears in the above-identified patent and that said Letters Patent are hereby corrected as shown below:

Column 1, line 29, "photoxicity" should be --phototoxicity--

Column 5, line 19, "$ZnCl_2$" should be --$ZnCl_3$--

Column 6, line 3, delete the hyphen "-" at end of line.

Column 6, line 12, "C, 50,16" should be --C, 50.16--.

Column 6, line 13, "C, 50,50" should be --C, 50.50--.

Column 7, line 2, delete "the" after "under".

Column 7, line 20, "compouund" should be --compound--.

Column 7, line 51 "Trifluoromethyphenyl" should be --Trifluoromethylphenyl--.

Column 8, line 37, "$(MgSO)_4$" should be --$(MgSO_4)$--

Column 9, line 10, "fluoromethyl" should be --fluoromethylphenyl--

Column 10, line 36, "$C_{25}H_{32}F_6N_2O$" should be --$C_{25}H_{32}F_6N_2O$--.

Column 10, line 62, change commas in C, 57,70 and H, 2,82 to read --C, 57.70 and H, 2.82--.

UNITED STATES PATENT OFFICE
CERTIFICATE OF CORRECTION

PATENT NO. : 3,940,404            Page 2 of 2

DATED : February 24, 1976

INVENTOR(S) : Arthur B. Ash, Maurice P. LaMontagne & Anica Markovac

It is certified that error appears in the above-identified patent and that said Letters Patent are hereby corrected as shown below:

Column 10, line 65, "$O_2$" should be --$PtO_2$--.

Column 11, line 2, "cruude" should be --crude--.

Column 12, line 59, Claim 1, insert "acceptable" after "pharmaceutically",

Signed and Sealed this

Seventeenth Day of August 1976

[SEAL]

Attest:

RUTH C. MASON
*Attesting Officer*

C. MARSHALL DANN
*Commissioner of Patents and Trademarks*